(12) United States Patent
Döring et al.

(10) Patent No.: US 8,426,483 B2
(45) Date of Patent: Apr. 23, 2013

(54) METAL COMPOUNDS FOR USE AS INITIATORS

(75) Inventors: Manfred Döring, Wörth (DE); Ulrich Arnold, Bruchsal (DE); Marcel Roth, Düsseldorf (DE); Emilie Barriau, Düsseldorf (DE); Ulrike Schmidt-Freytag, Düsseldorf (DE); Volker Alstädt, Rosengarten (DE); Felipe Wolff Fabris, Bayreuth (DE); Jan Sandler, Hanhofen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 616 days.

(21) Appl. No.: 12/515,763

(22) PCT Filed: Oct. 18, 2007

(86) PCT No.: PCT/EP2007/061158
§ 371 (c)(1),
(2), (4) Date: Dec. 10, 2009

(87) PCT Pub. No.: WO2008/064959
PCT Pub. Date: Jun. 5, 2008

(65) Prior Publication Data
US 2010/0113639 A1 May 6, 2010

(30) Foreign Application Priority Data

Dec. 1, 2006 (DE) .......................... 10 2006 057 142

(51) Int. Cl.
C07F 1/10 (2006.01)

(52) U.S. Cl.
USPC .............. 522/66; 522/170; 502/154; 502/155

(58) Field of Classification Search .................... 522/66, 522/170; 502/154, 155
See application file for complete search history.

(56) References Cited

U.S. PATENT DOCUMENTS

| 3,824,220 | A | * | 7/1974 | Smith et al. .................... 528/408 |
| 3,997,563 | A | | 12/1976 | Dale et al. |
| 4,624,912 | A | | 11/1986 | Zweifel et al. |
| 5,089,536 | A | | 2/1992 | Palazzotto |
| 5,614,126 | A | | 3/1997 | Gruber et al. |
| 5,726,216 | A | | 3/1998 | Janke et al. |
| 6,133,335 | A | | 10/2000 | Mahoney et al. |
| 2004/0176623 | A1 | | 9/2004 | Son et al. |
| 2012/0094137 | A1 | * | 4/2012 | Farrell et al. .................. 428/522 |

FOREIGN PATENT DOCUMENTS

| DE | 2523542 | 12/1975 |
| DE | 19534664 | 3/1997 |
| EP | 0153904 | 9/1988 |
| EP | 01482744 | 8/1992 |
| EP | 0388837 | 4/1996 |
| EP | 0843685 | 9/2003 |
| EP | 1416528 | 5/2004 |
| WO | WO9808906 | 3/1998 |

OTHER PUBLICATIONS

H.W. Quinn et al., "Coordination Compounds of Olefins With Anhydrous Silver Tetrafluoroborate V. Complexes With Some Cyclic di- and Oligo-Olefins"; Canadian Journal of Chemistry; vol. 48; pp. 2435-2437; 1970.
A.Albinati, et al., "The Crystal Structure of the Olefin Complex Di-1,5-Cyclooctadienesilver Tetrafluoroborate"; Journal of Organometallic Chemistry; vol. 182; pp. 269-274; 1979.
H. Masuda, "Raman Spectra of Copper(I) and Silver(I) Complexes With 1,5-Cyclooctadien and the Nature of Metal-Olefin Bonds. Possibility of a Copper(I)-Olefin Bond in Cytochrome Oxidase"; Journal of Organometallic Chemistry; vol. 391; pp. 131-137; 1990.
A.J. Canty et al., "π-Bonded Alkene and Arene Complexes of Silver(I): An Electrospray Mass Spectrometric Study"; Inroganica Chimica Acta; vol. 220; pp. 99-105; 1994.
STN-Datentbank Registry, vollständiger Eintrag zur Registry-Nr. (RN) 220612-44-2 (recherchiert am Feb. 7, 2007).
STN-Datentbank Registry, vollständiger Eintrag zur Registry-Nr. (RN) 33221-06-6 (recherchiert am Feb. 7, 2007).
STN-Datentbank Registry, vollständiger Eintrag zur Registry-Nr. (RN) 61577-46-6 (recherchiert am Feb. 7, 2007).

* cited by examiner

*Primary Examiner* — Margaret Moore
(74) *Attorney, Agent, or Firm* — Steven C. Bauman

(57) ABSTRACT

The present invention relates to initiators of the general formula $\{[M(L)_a]X_b\}_n$, wherein said initiators preferably have $(SbF_6^-)$ as a counterion and are obtainable by a complexing reaction of a corresponding metal-$SbF_6$ salt with a corresponding ligand (L). The present invention further relates to preparations and epoxy resin systems that contain such initiators and, in particular, are non-thermally and/or thermally curable.

12 Claims, No Drawings

METAL COMPOUNDS FOR USE AS INITIATORS

The present invention relates to initiators of the general formula $\{[M(L)_a]X_b\}_n$, these preferably having $(SbF_6^-)$ as a counterion and by preference being obtainable by the complexing reaction of a corresponding metal-$SbF_6$ salt with a corresponding ligand (L). The present invention further relates to preparations and to epoxy resin systems that contain such initiators and are, in particular, non-thermally and/or thermally curable.

In the manufacture of materials and coating substances, the curing rate is becoming increasingly important in many processes.

In the development of materials and coating substances, it is often desirable for the system to polymerize as quickly as possible so as to enable a high production rate or short cycle times.

In the context of polymerization, the initiators that initiate the curing reactions are therefore of particular significance. For example, initiators should be usable at room temperature and should produce rapid curing, but nevertheless not negatively influence the mechanical properties of the products.

In addition, the initiators should also meet certain requirements such as good solubility in the monomer, and shelf stability. The initiators should also exhibit no secondary effects such as yellowing of the product.

For some years, curable resins in particular have been cured by radiation energy. Polymerization (curing) can thus be initiated not only thermally but also by means of radiation energy. In the case of UV curing in particular, it often happens that the resin cures only in the regions that are exposed to a certain quantity of radiation energy. Complete curing of the resin depends on layer thickness: the radiation is attenuated upon penetration through the resin, or the radiation is largely attenuated or absorbed, for example, in the presence of a substance that is capable of absorbing a wavelength corresponding to that of the radiation energy.

The result is therefore that it is difficult, in the context of a curing operation, to reach the more deeply located portion of the resin.

It is therefore important in the context of curing by radiation, especially with resin systems, to use initiators that are activated quickly and, in particular, quickly generate a sufficient number of radicals, cations, and/or anions for polymerization to occur spontaneously. Curing by way of electron beams is therefore becoming increasingly preferred in contrast to UV curing or thermal curing, since it does not have many of the disadvantages of UV curing or thermal curing.

U.S. Pat. No. 5,726,216 claims a method for manufacturing non-thermally cured epoxy resins in which diaryliodonium salts are used as cationic initiators, and curing is performed by means of high-energy ionizing radiation at a dose greater than 0.75 kilogray/sec.

EP 0843685 B1 claims a method for manufacturing a toughness-modified, non-thermally curing epoxy resin system that likewise contains a cationic initiator made up of a diaryliodonium salt, and in which curing is carried out at a dose rate of more than 1 kilogray/sec.

The curing of epoxy resins usually occurs in the existing art in the presence of catalysts, which in most cases are made up of iodonium salts or sulfonium salts with the anions $SbF_6^-$, $AsF_6^-$, $PF_6^-$, or $BF_4^-$.

It was therefore an object of the present invention to discover and make available alternative initiators to those already known from the existing art.

A particular object of the present invention was to make available initiators that are easily manufacturable.

A further object of the present invention was to make available initiators that sufficiently cure a system, preferably a resin system, (in) non-thermally and/or thermally (initiated fashion), and exhibit a high degree of crosslinking after curing. Curing with the initiators according to the present invention is intended in particular not to negatively influence the thermomechanical and mechanical properties of the cured product.

A further object of the present invention was therefore to make available preparations as well as resin system, in particular epoxy resin systems, that contain the initiators according to the present invention.

Good shelf stability for the formulations and preparations that contain such initiators is a particularly important factor in this context.

It has been found, surprisingly, that initiators of the general formula (I)

$$\{[M(L)_a]X_b\}_n \qquad (I),$$

where M=metal cation, L=ligand, X=counterion,
a=1 to 10, preferably 1 to 6, particularly preferably 1 to 4,
b=1 to 10, preferably 1 to 6, particularly preferably 1 to 3,
n=1 to ∞,
wherein a, b, and n can represent both integers and number ranges, and a can also additionally represent non-integers, meet the requirements of the stated objects.

It has been shown, for example, that the initiators according to the present invention result in materials having very good values for modulus of elasticity (E).

It has moreover been shown that the initiators according to the present invention exhibit, in resins, a comparable and in some cases even improved crosslinking density as compared with initiator systems of the existing art.

The subject matter of the present invention is therefore initiators of the general formula (I)

$$\{[M(L)_a]X_b\}_n \qquad (I),$$

where M=metal cation, L=ligand, X=counterion,
a=1 to 10, preferably 1 to 6, particularly preferably 1 to 4,
b=1 to 10, preferably 1 to 6, particularly preferably 1 to 3,
n=1 to ∞,
wherein a, b, and n can represent both integers and number ranges, and a can also additionally represent non-integers.

In this context, the counterion (X) is preferably selected from hexafluoroantimonate $(SbF_6^-)$, hexafluorophosphate $(PF_6^-)$, boron tetrafluoride $(BF_4^-)$, hexafluoroaluminate $(AlF_6^{3-})$, trifluoromethanesulfonate $(CF_3SO_3^-)$, nitrate $(NO_3^-)$, hexafluoroarsenate $(AsF_6^-)$, tetrakis(pentafluorophenylborate) $(B[C_6F_5]_4^-)$, tetrakis[3.5-bis(trifluoromethyl)phenyl]borate $(B[C_6H_3(CF_3)_2]_4^-)$, tetraphenylborate $(B[C_6H_5]_4^-)$, hexafluorotitanate $(TiF_6^{2-})$, hexafluorogermanate $(GeF_6^{2-})$, hexafluorosilicate $(SiF_6^{2-})$, hexafluoronickelate $(NiF_6^{2-})$, or hexafluorozirconate $(ZrF_6^{2-})$. Hexafluoroantimonate $(SbF_6^-)$ is particularly preferred as a counterion (X).

A further subject of the present invention is initiators encompassing at least one metal cation (M), at least one ligand (L), and at least one molecule of hexafluoroantimonate $(SbF_6^-)$ as counterion, obtainable by the complexing reaction of a corresponding metal-$SbF_6$ salt with a corresponding ligand (L). In a preferred embodiment, the corresponding metal-$SbF_6$ salt is formed even before the complexing reaction with the corresponding ligand (L).

By preference, at least one reaction product of the complexing reaction encompasses a complex of the general formula (II)

$$\{[M(L)_a](SbF_6)_b\}_n \qquad (II),$$

where M=metal cation, L=ligand,
a=1 to 10, preferably 1 to 6, particularly preferably 1 to 4,
b=1 to 10, preferably 1 to 6, particularly preferably 1 to 3,
n=1 to ∞,
wherein a, b, and n can represent both integers and number ranges, and a can also additionally represent non-integers.

In a preferred embodiment, the metal cation (M) of the initiators (I) and/or (II) according to the present invention can be selected from the group of the transition metals of the fourth or fifth period or of the second or third main group of the periodic system. Particularly preferably, the metal cation (M) is selected from the group encompassing Ag, Fe, Mg, Co, Cu, Al, or Ti.

In a preferred embodiment, the ligand (L) is a compound having at least one (C—C) double and/or triple bond, preferably a substituted or unsubstituted, branched or unbranched, cyclic or non-cyclic alkene or alkine having 1 to 30 carbon atoms.

In a further preferred embodiment, the ligand (L) is an ether, in particular a cyclic ether, by preference a crown ether.

In a further preferred embodiment, the ligand (L) is a compound from the group of the nitriles. Such a compound encompasses at least one C≡N group.

Suitable preferred ligands (L) are selected, for example, from propene, 1-butene, 1-pentene, 1-hexene, 1-octene, 1-decene, isoprene, norbornene, cyclohexene, cyclooctene, cyclodecene, 1,4-cyclohexadiene, 4-vinylcyclohexene, trans-2-octene, styrene, 5-norbornene-2-carboxylic acid, butadiene, 1,5-hexadiene, 1,6-heptadiene, 1,7-octadiene, 1,9-decadiene, sorbic acid ethyl ester, 1,3-cyclohexadiene, 1,3-cyclooctadiene, 1,5-cyclooctadiene, norbornadiene, dicyclopentadiene, cycloheptatriene, trans,trans,trans-1,5,9-cyclododecatriene, trans,trans,cis-1,5,9-cyclododecatriene, cyclooctatetraene, squalene, diallyl carbonate, diallyl ether, diallyldimethylsilane, nopol, cyclopentadiene, ethyl vinyl ether, limonene, 1,2-dihydronaphthalene, cinnamic acid ethyl ester, ethyl acrylate, ethyl methacrylate, stilbene, oleic acid methyl ester, linoleic acid methyl ester, linolenic acid methyl ester, diphenylacetylene, dimethylacetylene, 3-hexine, 1,8-cyclotetradecadiine, propargyl alcohol, vinylacetylene, 15-crown-5,18-crown-6,1-phenylpropine, 1,8-nonadiine, 18-crown-6-tetracarboxylic acid.

According to the present invention, a, b, and n can represent both integers and number ranges, and a can, additionally, also represent non-integers. Particularly preferably, a is a number range from 1 to 6, particularly preferably from 1 to 4. More preferably, a=1, 1.5, 2, 3, or 4, very particularly preferably 1, 1.5, or 2. Particularly preferably, b is a number range from 1 to 6, particularly preferably from 1 to 3. More preferably, b=1, 2, 3, or 4, very particularly preferably 1, 2, or 3.

n is preferably either 1 (monomeric metal complex) or preferably lies in a range from 1 to ∞ (monomeric, dimeric, trimeric, oligomeric, and polymeric coordination compounds or mixtures thereof), for example preferably 1 to 20,000, particularly preferably 1 to 1000, very particularly preferably 1 to 500 or 1 to 300. Particularly preferred for n, however, is a number range between 1 and ∞ (infinity).

Because the initiators according to the present invention can, in the case of multifunctional ligands L (dienes, trienes, oligoalkenes, diines, oligoalkines), represent coordination polymers, "∞" in the present invention means that n can proceed into infinity.

If n=1, this means according to the present invention that monomeric coordination compounds are present. If n is a number range from 1 to ∞, this means that in addition to monomeric coordination compounds, dimeric, trimeric, oligomeric, and polymeric coordination compounds (so-called coordination polymers), and mixtures thereof having different chain lengths, can also be present.

In a preferred embodiment, a mixture of initiators of the general formula (I) is therefore present; particularly preferably, a mixture of initiators of the general formula (II) is present.

A prerequisite for the formation of dimeric, trimeric, and oligomeric coordination compounds and coordination polymers is multifunctional ligands L that are capable of linking multiple metal centers and thus enabling the construction of dimeric, trimeric, oligomeric, and polymeric structures. This is not possible with monoalkenes and -alkines and crown ethers, and exclusively mononuclear coordination compounds, i.e. monomeric complexes having only one metal center, are preferably obtained (parameters a and b are variable; n=1). In the case of cyclic di-, tri-, or tetraenes (e.g. 1,5-cyclooctadiene, cycloheptatriene, or cyclooctatetraene), predominantly mononuclear metal complexes are preferably obtained, but the formation of polynuclear ligand-bridged structures is also possible. If open-chain dienes are used as ligands L, the formation of coordination polymers can also be favored depending on the metal cation and anion. For example, if AgSbF$_6$ is reacted with 1,7-octadiene, then preferably $\{[Ag(1,7\text{-octadiene})_{1.5}]SbF_6\}_\infty$ is obtained, a coordination polymer having, for example, a one-dimensional chain structure (a=1.5, b=1, n=∞) in which the silver centers are preferably bridged alternately by one and two molecules of 1,7-octadiene:

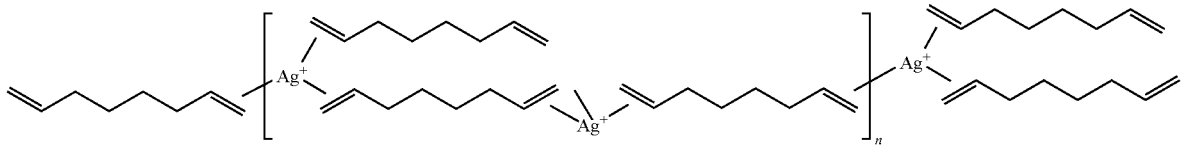

The ligands 1,5-hexadiene and 1,9-decadiene preferably yield similar structures. As the number of double bonds in the ligand increases, more and more branching possibilities occur, the resulting structures become preferably more complex, and mixtures of differently crosslinked oligomeric and polymeric coordination compounds are preferably obtained, for example an open-chain hexaalkene in the case of squalene as the ligand. By preference, in addition to mononuclear compounds, polynuclear compounds are also formed.

Initiators according to the present invention are [Ag(cyclohexene)$_2$]SbF$_6$, [Ag(cyclooctene)$_{1-4}$]SbF$_6$, [Ag(cyclododecene)$_{1-4}$]SbF$_6$, [Ag(trans-2-octene)$_{1-4}$]SbF$_6$, [Ag(styrene)$_{1-4}$]SbF$_6$, [Ag(5-norbornene-2-carboxylic acid)$_{1-4}$]SbF$_6$, $\{[Ag(1,5\text{-hexadiene})_{1-4}]SbF_6\}_{1-\infty}$, $\{[Ag(1,7\text{-octadiene})_{1.5}]SbF_6\}_\infty$, $\{[Ag(1,7\text{-octadiene})_{1.5}]SbF_6\}_{1-\infty}$, {[Ag(1,7-octadiene)$_{1.5}$]SbF$_6$}$_{500}$, {[Ag(1,9-decadiene)$_{1-4}$]SbF$_6$}$_{1-\infty}$, {[Ag(sorbic acid ethyl ester)$_{1-4}$]SbF$_6$}$_{1-\infty}$, {[Ag(1,3-cyclohexadiene)$_{1-4}$]SbF$_6$}$_{1-28}$, {[Ag(1,3-cyclooctadiene)$_{1-4}$]SbF$_6$}$_{1-\infty}$, [Ag(1,5-cyclooctadiene)$_2$]SbF$_6$, {[Ag(norbornadiene)$_{1-4}$]SbF$_6$}$_{1-\infty}$, {[Ag(dicyclopentadiene)$_{1-4}$]SbF$_6$}$_{1-\infty}$, {[Ag(cycloheptatriene)$_{1-4}$]SbF$_6$}$_{1-\infty}$, {[Cu(1,7-octadiene)$_{1-4}$]SbF$_6$}$_{1-\infty}$, [Cu(1,5-cyclooctadiene)$_2$]SbF$_6$, [Cu(15-crown-5)]SbF$_6$, [Fe(15-crown-5)](SbF$_6$)$_3$, [Fe(18-crown-6)](SbF$_6$)$_3$, [Mg(15-crown-5)](SbF$_6$)$_2$, [Co(15-crown-5)](SbF$_6$)$_2$, [Ag(1R-(-)-nopol)$_{1-4}$]SbF$_6$, [Ag(allyl glycidyl ether)$_{1-4}$]SbF$_6$, {[Ag(trans,trans,cis-1,5,9-cyclododecatriene)$_{1-4}$]SbF$_6$}$_{1-\infty}$, {[Ag(trans,trans,trans-1,5,9-cyclododecatriene)$_{1-4}$]SbF$_6$}$_{1-\infty}$, {[Ag(cyclooctatetraene)$_{1-4}$]SbF$_6$}$_{1-\infty}$, {[Ag(squalene)$_{1-4}$]SbF$_6$}$_{1-\infty}$.

The initiators according to the present invention preferably initiate polymerization by forming cations.

In a preferred embodiment, the initiators according to the present invention are also photoinitiators.

A further subject of the present invention is preparations that contain at least one initiator according to the present invention.

The term "preparation" denotes, in the context of the present invention, mixtures containing at least one initiator according to the present invention and at least one further additive that either is present because of the manner of manufacture of the initiators according to the present invention (for example solvents, catalysts), or is mixed in subsequently (e.g. plasticizers, reactive diluents, fillers, and the like).

Accordingly, the preparation according to the present invention preferably contains one or more additional constituents (additives) that are selected from the group of the fillers, stabilizers, hardener accelerators, antioxidants, adhesion promoters, rheology agents, thickeners, binders, solvents, radical scavengers, catalysts, reactive diluents, plasticizers, additive resins, flame protection additives, impact additives such as, for example, elastomers, thermoplastics, core-shell particles, nanoparticles, block copolymers, nanotubes. Depending on the intended end use, further usual additives such as dispersants, anti-scratch agents, pigments, dyes, emulsifiers (surfactants), corrosion inhibitors can be added to the preparations according to the present invention.

The concentration of the initiators according to the present invention in the preparations is by preference 0.01 to 10 wt %, preferably 0.5 to 3 wt %, and particularly preferably 1 to 2 wt %, based on the entire composition.

Suitable as plasticizers are, for example, by preference esters such as abietic acid esters, adipic acid esters, azelaic acid esters, benzoic acid esters, butyric acid esters, acetic acid esters, phosphoric acid esters, phthalic acid esters; esters of higher fatty acids having approximately 8 to approximately 44 carbon atoms, such as dioctyl adipate, diisodecyl succinate, dibutyl sebacate or butyloleate, esters of OH-group-carrying or epoxidized fatty acids, fatty acid esters, and fats, glycolic acid esters, phosphoric acid esters, phthalic acid esters of linear or branched alcohols containing 1 to 12 carbon atoms such as, for example, dioctyl phthalate, dibutyl phthalate, or butylbenzyl phthalate, propionic acid esters, sebacic acid esters, sulfonic acid esters, thiobutyric acid esters, trimellitic acid esters, citric acid esters, and esters based on nitrocellulose and polyvinyl acetate, as well as mixtures of two or more thereof. The asymmetrical esters of the difunctional aliphatic dicarboxylic acids are particularly suitable, for example the esterification product of adipic acid monooctyl ester with 2-ethylhexanol (Edenol DOA, Henkel Co., Düsseldorf).

Also suitable as plasticizers are, preferably, the pure or mixed ethers of monofunctional, linear, or branched C$_{4-16}$ alcohols or mixtures of two or more different ethers of such alcohols, for example dioctyl ether (obtainable as Cetiol OE, Henkel Co., Düsseldorf).

In a further preferred embodiment, end-capped polyethylene glycols are used as plasticizers, for example polyethylene or polypropylene glycol di-C1-4-alkyl ethers, in particular the dimethyl or diethyl ethers of diethylene glycol or dipropylene glycol, as well as mixtures of two or more thereof.

The preparation according to the present invention can contain up to approximately 80 wt % fillers. Inorganic fillers are suitable as fillers, for example naturally occurring or synthetic materials such as, for example, quartz, nitrides (e.g. silicon nitride), glasses derived e.g. from Ce, Sb, Sn, Zr, Sr, Ba, and Al, colloidal silicon dioxide, feldspar, borosilicate glasses, kaolin, talc, titanium dioxide, and zinc glasses, as well as sub-micron-size silicon dioxide particles (e.g. pyrogenic silicon dioxides such as, for example, the silicon dioxides of the "Aerosil" "OX 50", "130", "150", and "200" series that are sold by Degussa, as well as "Cab-O-Sil M5" that is sold by Cabot Corp.), aluminum silicates, magnesium silicates, zeolites, bentonites, ground mineral substances, calcium carbonates, quartz dust, silicic acid anhydride, silicon hydrate or carbon black, magnesium carbonate, fired clay, clay, iron oxide, zinc oxide, titanium dioxide, cellulose, wood flour, mica, chaff, graphite, fine aluminum powder or flint powder, glass spheres, glass powder, glass fiber and chopped glass fibers, as well as further inorganic fillers known to one skilled in the art, as well as organic fillers, in particular chopped fibers or hollow plastic spheres, as well as functional fillers that positively influence rheological properties, for example highly dispersed silicic acid, in particular having a low BET surface area from 20 to 150, preferably 30 to 100, particularly preferably approximately 50 m$^2$/g. In some cases it is possible to use fillers that impart thixotropy to the preparation, for example swellable plastics such as PVC.

Suitable additive resins are all natural and synthetic resins such as, for example, colophonium derivatives (e.g. derivatives resulting from disproportionation, hydrogenation, or esterification), cumarone-indene and polyterpene resins, aliphatic or aromatic hydrocarbon resins (C-5, C-9, (C-5)2 resins), mixed C-5/C-9 resins, hydrogenated and partly hydrogenated derivatives of the aforesaid types, resins from styrene or α-methylstyrene, as well as terpene-phenol resins, and others as set forth in Ullmanns Enzyklopädie der technischen Chemie [Encyclopedia of chemical engineering] (4th ed.), vol. 12, pp. 525-555, Weinheim.

Suitable solvents are ketones, lower alcohols, lower carboxylic acids, ethers and esters such as (meth)acrylic acid (esters), acetone, acetylacetone, acetoacetic esters, methyl ethyl ketone, methyl isobutyl ketone, cyclopentanone, cyclohexanone, n-methylpyrrolidone, dioxan, tetrahydrofuran, 2-methoxyethanol, 2-ethoxyethanol, 1-methoxy-2-propanol, 1,2-dimethoxyethane, ethyl acetate, n-butyl acetate, ethyl-3-ethoxypropionate, methanol, ethanol, isopropanol, n-propanol, n-butanol, isobutanol, sec.-butanol, tert.-butanol, diacetone alcohol, 2-ethylhexyl alcohol, ethylene glycol, diethylene glycol, ethylene glycol dimethyl ether, ethylene glycol diethyl ether, ethylene glycol di-n-butyl ether, diethylene glycol, diethylene glycol dimethyl ether, diethylene glycol diethyl ether, diethylene glycol di-n-butyl ether, polyethylene glycols, formic acid, acetic acid, or propionic acid, THF, dioxan, acetonitrile, propionitrile, dimethylformamide, dimethylsulfoxide, sulfolane, dimethyl carbonate, diethyl carbonate, di-n-butyl carbonate, 1,2-ethylene carbonate, 1,2-propylene carbonate, or 1,3-propylene carbonate, and aromatic hydrocarbons such as toluene and xylene.

The α-silanes preferred as adhesion promoters and/or reactive diluents are advantageously selectable from the group made up of α-methacrylsilanes, α-carbamatosilanes, and α-alkoxysilanes. Suitable examples are (methacryloxymethyl)methyldiethoxysilane and methacryloxymethyltriethoxysilane, N-(triethoxysilylmethyl)-O-methyl carbamate, and N-(methyldiethoxysilylmethyl)-O-methyl carbamate. Appropriate thickeners, in addition to radically (co)polymerized (co)polymerizates, are usual organic and inorganic thickeners such as hydroxymethyl cellulose or bentonite. Suitable catalysts for promoting crosslinking are, in particular, morpholine, N-methylmorpholine, 1,3-diazabicyclo[5.4.6]undecene-7 (DBU). Further suitable catalysts are those based on organic or inorganic heavy-metal compounds such as, for example, cobalt naphthenate, dibutyltin dilaurate, tin mercaptide, tin dichloride, zirconium tetraoctoate, tin naphthenate, tin stearate, antimony dioctoate, lead dioctoate, metal, in particular iron acetylacetonate. All catalysts known for the acceleration of silanol condensation are especially appropriate. These are, for example, organotin, organotitanium, organozirconium, or organoaluminum compounds. Examples of such compounds are dibutylin dilaurate, dibutyltin dimaleate, tin octoate, isopropyltriisostearoyl titanate, isopropyltris(dioctylpyrophosphate) titanate, bis(dioctylpyrophosphate) oxyacetate titanate, tetrabutyl zirconate, tetrakis(acetylacetonato)zirconium, tetraisobutyl zirconate, butoxytris(acetylacetonato)zirconium, tris(ethylacetoacetato)aluminum. Dibutyltin alkyl esters such as dibutyltin alkyl maleates or dibutyltin laurates are particularly suitable, in particular dibutyltin bisethyl maleate, dibutyltin bisbutyl maleate, dibutyltin bisoctylmaleate, dibutyltin bisoleyl maleate, dibutyltin bisacetyl acetate, dibutyltin diacetate, dibutyltin dioctoate, dibutyltin oxide, dibutyltin bistriethoxysilicate, and catalytically effective derivatives thereof. The aforesaid catalysts can be used alone or as a mixture of two or more of the aforesaid catalysts.

The preparations according to the present invention can contain up to 5 wt % of such catalysts in the entire composition.

The preparations according to the present invention can furthermore contain up to approximately 7 wt %, in particular approximately 3 to approximately 5 wt %, antioxidants in the entire composition.

Included among the stabilizers or antioxidants usable in the context of the invention as additives are hindered phenols of high molecular weight ($M_w$), polyfunctional phenols, and sulfur- and phosphorus-containing phenols. Phenols usable in the context of the invention as additives are, for example, 1,3,5-trimethyl-2,4,6-tris(3,5-di-tert-butyl-4-hydroxybenzyl)benzene; pentaerythritol tetrakis-3-(3,5-di-tert-butyl-4-hydroxyphenyl) propionate; n-octadecyl-3,5-di-tert-butyl-4-hydroxyphenyl) propionate; 4,4-methylenebis(2,6-di-tert-butylphenol); 4,4-thiobis(6-tert-butyl-o-cresol); 2,6-di-tert-butylphenol; 2,4-dimethyl-6-tert-butylphenol, 2,2'-methylene-bis-(4-methyl-6-tert-butylphenol; 4,4'-butylidene-bis-(3-methyl-6-tert-butylphenol); 4,4'-thiobis(3-methyl-6-tert-butylphenol); 2,6-di-tert-butyl-p-cresol; 6-(4-hydroxyphenoxy)-2,4-bis(n-octylthio)-1,3,5-triazine; tetrakis[methylene-3-(3,5-di-tert-butyl-4-hydroxyphenyl) propionate]methane; 1,1,3-tris(2-methyl-4-hydroxy-4-tert-butylphenyl)butane; di-n-octadecyl-3,5-di-tert-butyl-4-hydroxybenzyl phosphonate; 2-(n-octylthio)ethyl-3,5-di-tert-butyl-4-hydroxybenzoate; and sorbitol hexa[3-(3,5-di-tert-butyl-4-hydroxyphenyl) propionate].

Suitable photostabilizers are, for example, those obtainable commercially under the name Tinuvin® (manufacturer: Ciba Geigy).

Suitable stabilizers, which are typically UV absorbers and represent light stabilizers, can likewise be contained, selected by preference from the groups of the oxanilides, triazines, and benzotriazoles (the latter obtainable as Tinuvin® brands of Ciba Specialty Chemicals) and benzophenones, or combinations thereof. It may be advantageous to add light stabilizers that do not absorb UV light.

A selection of suitable preferred UV absorbers and light stabilizers that can be contained in the preparations according to the present invention are: 2-hydroxybenzophenones, for example the 4-hydroxy, 4-methoxy, 4-octyloxy, 4-decyloxy, 4-dodecyloxy, 4-benzyloxy, 4,2',4'-trihydroxy, and 2'-hydroxy-4,4'-dimethoxy derivatives; esters of substituted and unsubstituted benzoic acids such as, for example, 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl-3,5-di-tert-butyl-4-hydroxybenzoate, hexadecyl-3,5-di-tert-butyl-4-hydroxybenzoate, octadecyl-3,5-di-tert-butyl-4-hydroxybenzoate, 2-methyl-4,6-di-tert-butylphenyl-3,5-di-tert-butyl-4-hydroxybenzoate.

The preparations according to the present invention can contain up to approximately 2 wt %, by preference approximately 1 wt % of such UV stabilizers in the entire composition.

The preparations according to the present invention can furthermore contain impact additives (impact modifiers).

Suitable impact additives are, for example, terminally functionalized or non-terminally functionalized thermoplastics such as polysulfones, polyphenylsulfones, polyethersulfones (e.g. Radel and Udel of Solvay, or Ultrason of BASF), polyether ether ketones, polyether ketones, polybutylene terephthalates, polycarbonates, polyether imides, polyethylene, nylon, polyamide imides, poly(aryl ethers), polyesters, polyarylates.

Suitable elastomers that likewise function as impact modifiers are, for example, EPDM or EPM rubber, polyisobutylene, butyl rubber, ethylene-vinyl acetate, hydrogenated block copolymers made of dienes (e.g. by the hydrogenation of SBR, cSBR, SBS, SIS, IR; such polymers are known, for example, as SEPS and SEBS), copolymers of styrene, butadiene, and ethylene, or styrene, butylene, ethylene, butadiene, butyl rubber, neoprene rubber, and poly(siloxanes).

Polymers having a molecular weight from approximately 5000 to 2,000,000, by preference 10,000 to 1,000,000, such as preferably homo- and copolymers of acrylates and methacrylates, copolymers of methyl methacrylate/ethyl acrylate/methacrylic acid, poly(alkyl methacrylates), poly(alkyl acrylates); cellulose esters and ethers such as cellulose acetate, cellulose acetobutyrate, methyl cellulose, ethyl cellulose; polyvinylbutyral, polyvinylformal, cyclized rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate, and vinyl acetate, polyvinyl acetate, copoly(ethylene/vinyl acetate), polymers such as polycaprolactam and poly(hexamethylene adipamide), polyesters such as poly(ethylene glycol terephthalate) and poly(hexamethylene glycol succinate), can also be used as impact additives.

Suitable nanoparticles that can likewise be used as impact modifiers are in particular those based on silicon dioxide (e.g. Nanopox of Nanoresins), aluminum oxide, zirconium oxide, and barium sulfate. They preferably have a particle size of less than 50 nm. Examples of suitable nanoparticles based on silicon dioxide are pyrogenic silicon dioxides that are marketed under the trade name Aerosil® VP8200, VP721, or R972 of the Degussa company or the trade name Cab O Sil® TS 610, CT 1110F, or CT 1110G of the Cabot company. "Multiwall" and "single wall" nanoparticles having a modified or unmodified surface are likewise usable.

Also conceivable are nanoparticles present in the form of dispersions, for example the dispersion marketed under the trade name High Link® OG 103-31 by the Clariant Hoechst company.

Suitable core-shell particles, which have e.g. a crosslinked silica core and a functionalized shell (e.g. Genioperl of Wacker, Albidur of Nanoresins) or that have, for example, a rubber core (e.g. Zeon, Kaneka), as well as suitable highly functionalized polymers, e.g. polyols, dendritic polymers (e.g. Boltorn of Perstorp), and polyesters, can likewise be used.

The preparations according to the present invention can contain up to 90 wt %, by preference up to 80 wt %, particularly preferably up to 50 wt % impact additives in the entire composition.

The preparations according to the present invention can furthermore contain thermal inhibitors, which are provided in order to prevent premature polymerization. Suitable inhibitors are, for example, hydroquinone, hydroquinone derivatives, p-methoxyphenol, β-naphthol, or sterically hindered phenols such as 2,6-di(tert-butyl)-p-cresol.

Suitable dispersants are water-soluble organic compounds having a high molecular weight that carry polar groups, for example polyvinyl alcohols, polyethers, polyvinylpyrrolidone, or cellulose ethers.

Suitable emulsifiers can be nonionic emulsifiers, and in some cases ionic emulsifiers can likewise be used.

It is additionally possible to use initiators known from the existing art in the preparations according to the present invention, in order to assist the polymerization that has been initiated by the initiators according to the present invention.

It is thus possible, for example, to add thermally activatable initiators selected from organic azo compounds, organic peroxides, C—C-cleaving initiators such as benzopinacol silyl ethers, hydroxyimides such as, for example, N-hydroxyphthalimide or N-hydroxysuccinimide. Included among the thermally activatable peroxo compounds that are suitable as initiators are representatives of the various peroxide compounds, such as disuccinoyl peroxide, potassium peroxodisulfate, cyclohexylsulfonylacetyl peroxide, dibenzoyl peroxide, cyclohexanone peroxide, di-tert-butyl peroxide, dialkyl peroxides, diacyl peroxides, peroxydicarbonates, perketals, peroxycarboxylic acids and esters thereof, ketone peroxides, and/or hydroperoxides. Di(3,5,5-trimethylhexanoyl) peroxide, didecanoyl peroxide, dilauroyl peroxide, dibenzoyl peroxide, di(2-ethylhexyl)peroxydicarbonate, dicyclohexylperoxydicarbonate, di(4-tert-butylcyclohexyl)peroxydicarbonate, dimyristylperoxydicarbonate, diacetylperoxydicarbonate, di-tert-butylperoxyoxalate are particularly preferred, as are peroxycarboxylic acid esters made up of the products of reaction between pivalic acid, neodecanoic acid, or 2-ethylhexanoic acid and tert-butyl hydroperoxide, tert-amyl hydroperoxide, cumyl hydroperoxide, 2,5-dimethyl-2,5-dihydroperoxyhexane, 1,3-di(2-hydroxyperoxyisopropyl)benzene.

Also appropriate is a system made up of two or more of the aforesaid thermally activatable initiators.

In a further embodiment, the initiators according to the present invention can be used in the preparation with other initiators. These can be, for example, photoinitiators known to one skilled in the art.

Suitable preferred photoinitiators are, for example, benzophenone, acetophenone, acetonaphthoquinone, methyl ethyl ketone, valerophenone, hexanophenone, α-phenylbutyrophenone, p-morpholinopropiophenone, dibenzosuberone, 4-morpholinobenzophenone, 4-morpholinodeoxybenzoin, p-diacetylbenzene, 4-aminobenzophenone, 4-methoxyacetophenone, β-methylanthraquinone, tert-butylanthraquinone, anthraquinonecarboxylic acid esters, benzaldehyde, α-tetralone, 9-acetylphenanthrene, 2-acetylphenanthrene, 10-thioxanthenone, 3-acetylphenanthrene, 3-acetylindole, 9-fluorenone, 1-indanone, 1,3,4-triacetylbenzene, thioxanthen-9-one, xanthen-9-one, 2,4-dimethylthioxanthone, 2,4-diethylthioxanthone, 2,4-diisopropylthioxanthone, 2,4-dichlorothioxanthone, benzoin, benzoin isobutyl ether, chloroxanthenone, benzoin tetrahydropyranyl ether, benzoin methyl ether, benzoin ethyl ether, benzoin butyl ether, benzoin isopropyl ether, 7-H-benzoin methyl ether, benz[de]anthracen-7-one, 1-naphthaldehyde, 4,4'-bis(dimethylamino)benzophenone, 4-phenylbenzophenone, 4-chlorobenzophenone, Michler's ketone, 1-acetonaphthone, 2-acetonaphthone, 1-benzoylcyclohexane-1-ol, 2-hydroxy-2,2-dimethylacetophenone, 2,2-dimethoxy-2-phenylacetophenone, 2,2-diethoxy-2-phenylacetophenone, 1,1-dichloroacetophenone, 1-hydroxyacetophenone, acetophenone dimethyl ketal, o-methoxybenzophenone, triphenylphosphine, tri-o-tolylphosphine, benz[a]anthracene-7,12-dione, 2,2-diethoxyacetophenone, benzyl ketals such as benzyl dimethyl ketal, 2-methyl-1-[4-(methylthio)phenyl]-2-morpholinopropan-1-one, anthraquinone such as 2-methylanthraquinone, 2-ethylanthraquinone, 2-tert-butylanthraquinone, 1-chloroanthraquinone, 2-amylanthraquinone, and 2,3-butanedione, 2,4,6-trimethylbenzoyldiphenylphosphine oxide (Lucirin® TPO of BASF AG), ethyl-2,4,6-trimethylbenzoylphenyl phosphinate (Lucirin® TPO L of BASF AG), bis-(2,4,6-trimethylbenzoyl)phenylphosphine oxide (Irgacure® 819 of Ciba Specialty Chemicals), benzophenones, hydroxyacetophenones, phenylglyoxylic acid, and derivatives thereof, or mixtures of said photoinitiators.

Accelerators for thermal post-curing that can be used in the preparations according to the present invention are by preference, for example, tin octoate, zinc octoate, dibutyltin laurate, or diaza[2.2.2]bicyclooctane.

In a further preferred embodiment, in addition to the initiators according to the present invention, a combination of a thermally activatable initiator and a photochemical initiator is additionally introduced into the preparations according to the present invention. This has the advantage that initiators that are optimized in terms of their utilization range can be used.

The preparation according to the present invention is by preference a resin system selected from the group of the epoxy resin systems, benzoxazine systems, polyurethane systems, acrylate resin systems, epoxy acrylate resin systems, cyanoacrylate resin systems, triazine resin systems, polyimide resin systems, ester acrylate resin systems, or thermoplastic resin systems. The preparation is preferably an epoxy resin system.

A mixture of the aforesaid resin systems can also be present. In this case a mixture of an epoxy resin system and a benzoxazine system and/or polyurethane system and/or acrylate resin system and/or an epoxy acrylate resin system is preferably present. The combination of an epoxy resin system and an acrylate resin system is particularly preferred.

An "epoxy resin system" is understood in the context of the present invention as a resin composition formed on the basis of epoxy compounds or epoxy-containing compounds.

Epoxy compounds or epoxy-containing compounds of this kind can encompass both oligomeric and monomeric epoxy compounds and epoxies of the polymeric type, and can represent aliphatic, cycloaliphatic, aromatic, or heterocyclic compounds. The epoxy compounds or epoxy-containing compounds of the epoxy resin system generally comprise, on average, at least one polymerizable epoxy group per molecule, by preference at least approximately 1.5 polymerizable epoxy groups per molecule. The polymeric epoxies encompass linear polymers having terminal epoxy groups (e.g. a diglycidyl ether of a polyoxyalkylene glycol), polymers having oxirane units in the molecular framework (e.g. polybutadiene polyepoxide), and polymers having epoxy groups appended to the framework (e.g. a glycidyl methacrylate polymer or copolymer). These epoxies can be pure compounds or mixtures that contain one, two, or more epoxy groups per molecule. The "average" number of epoxy groups per molecule is determined by dividing the total number of epoxy groups in the epoxy-containing material by the total number of epoxy molecules present.

The molecular weight of the epoxy compounds or epoxy-containing compounds of the epoxy resin systems varies from 100 g/mol to a maximum of 10,000 g/mol for polymeric epoxy resins. No limits are likewise set on the epoxy compounds or epoxy-containing compounds in terms of the nature of their basic framework and their substituent groups. For example, the basic framework can belong to any desired type, and the substituent groups present thereon can represent all groups that do not substantially interfere with curing. The substituent groups encompass, for example, halogens, ester groups, ethers, sulfonate groups, siloxane groups, nitro groups, phosphate groups, and the like.

Suitable epoxy resin systems in the context of the present invention are, for example, preferably selected from epoxy resins of the bisphenol A type, epoxy resins of the bisphenol S type, epoxy resins of the bisphenol F type, epoxy resins of the phenol novolac type, epoxy resins of the cresol novolac type, epoxidized products of numerous dicyclopentadiene-modified phenol resins obtainable by the reaction of dicyclopentadiene with numerous phenols, epoxidized products of 2,2',6,6'-tetramethylbiphenol, aromatic epoxy resins such as epoxy resins having a naphthalene basic framework and epoxy resins having a fluorene basic framework, aliphatic epoxy resins such as neopentyl glycol diglycidyl ethers and 1,6-hexanediol diglycidyl ethers, alicyclic epoxy resins such as 3,4-epoxycyclohexylmethyl-3,4-epoxycyclohexane carboxylate and bis(3,4-epoxycyclohexyl) adipate, and epoxy resins having a hetero ring, such as triglycidyl isocyanurate.

The epoxy resins encompass in particular, for example, the reaction product of bisphenol A and epichlorohydrin, the reaction product of phenol and formaldehyde (novolac resins) and epichlorohydrin, glycidyl esters, and the reaction product of epichlorohydrin and p-aminophenol.

Further preferred epoxy resins that are commercially obtainable encompass, in particular, octadecylene oxide, epichlorohydrin, styrene oxide, vinylcyclohexene oxide, glycidol, glycidyl methacrylate, diglycidyl ethers of bisphenol A (e.g. those obtainable under the commercial designations "Epon 828", "Epon 825", "Epon 1004" and "Epon 1010" of Hexion Specialty Chemicals Inc., "DER-331", "DER-332", "DER-334", "DER-732" and "DER-736" of Dow Chemical Co.), vinylcyclohexene dioxide, 3,4-epoxycyclohexylmethyl-3,4-epoxycyclohexene carboxylate, 3,4-epoxy-6-methylcyclohexylmethyl-3,4-epoxy-6-methylcyclohexane carboxylate, bis(3,4-epoxy-6-methylcyclohexylmethyl) adipate, bis(2,3-epoxycyclopentyl)ether, aliphatic epoxide modified with polypropylene glycol, dipentene dioxide, epoxidized polybutadiene (e.g. Krasol products of Sartomer), silicone resins containing epoxide functionality, flame-retardant epoxy resins (e.g. "DER-580", a brominated epoxy resin of the bisphenol type obtainable from Dow Chemical Co.), 1,4-butanediol diglycidyl ethers of a phenol/formaldehyde novolac (e.g. "DEN-431" and "DEN-438" of the Dow Chemical Co.), as well as resorcinol diglycidylethers (e.g. "Kopoxite" of the Koppers Company Inc.), bis(3,4-epoxycyclohexyl) adipate, 2-(3,4-epoxycyclohexyl-5,5-spiro-3,4-epoxy)cyclohexane-meta-dioxan, vinylcyclohexene monoxide, 1,2-epoxyhexadecane, alkyl glycidyl ethers such as, for example, C8-C10-alkyl glycidyl ethers (e.g. "HELOXY Modifier 7" of Hexion Specialty Chemicals Inc.), C12-C14-alkyl glycidyl ethers (e.g. "HELOXY Modifier 8" of Hexion Specialty Chemicals Inc.), butyl glycidyl ethers (e.g. "HELOXY Modifier 61" of Hexion Specialty Chemicals Inc.), cresyl glycidyl ethers (e.g. "HELOXY Modifier 62" of Hexion Specialty Chemicals Inc.), p-tert-butylphenyl glycidyl ethers (e.g. "HELOXY Modifier 65" of Hexion Specialty Chemicals Inc.), polyfunctional glycidyl ethers such as, for example, diglycidyl ethers of 1,4-butanediol (e.g. "HELOXY Modifier 67" of Hexion Specialty Chemicals Inc.), diglycidyl ethers of neopentyl glycol (e.g. "HELOXY Modifier 68" of Hexion Specialty Chemicals Inc.), diglycidyl ethers of cyclohexanedimethanol (e.g. "HELOXY Modifier 107" of Hexion Specialty Chemicals Inc.), trimethylolethane triglycidyl ethers (e.g. "HELOXY Modifier 44" of Hexion Specialty Chemicals Inc.), trimethylolpropane triglycidyl ethers (e.g. "HELOXY Modifier 48" of Hexion Specialty Chemicals Inc.), polyglycidyl ethers of an aliphatic polyol (e.g. "HELOXY Modifier 84" of Hexion Specialty Chemicals Inc.), polyglycol diepoxide (e.g. "HELOXY Modifier 32" of Hexion Specialty Chemicals Inc.), bisphenol F epoxies (e.g. "EPN-1138" or "GY-281" of Huntsman Int. LLC), 9,9-bis-4-(2,3-epoxypropoxy)phenylfluorenone (e.g. "Epon 1079" of Hexion Specialty Chemicals Inc.).

Further preferred commercially obtainable compounds are selected, for example, from Araldite™ 6010, Araldite™ GY-281™, Araldite™ ECN-1273, Araldite™ ECN-1280, Araldite™ MY-720, RD-2 of Huntsman Int. LLC; DEN™ 432, DEN™ 438, DEN™ 485 of Dow Chemical Co., Epon™ 812, 826, 830, 834, 836, 871, 872, 1001, 1031 etc. of Hexion Specialty Chemicals Inc. and HPT™ 1071, HPT™ 1079 likewise of Hexion Specialty Chemicals Inc., as novolac resins furthermore, for example, Epi-Rez™ 5132 of Hexion Specialty Chemicals Inc., ESCN-001 of Sumitomo Chemical, Quatrex 5010 of Dow Chemical Co., RE 305S of Nippon Kayaku, Epiclon™ N673 of DaiNipon Ink Chemistry, or Epicote™ 152 of Hexion Specialty Chemicals Inc. Melamine resins can also be used as reactive resins, e.g. Cymel™-327 and -323 of Cytec.

Terpene-phenol resins can also be used as reactive resins, for example NIREZ™ 2019 of Arizona Chemical.

Phenol resins can also be used as reactive resins, for example YP 50 of Toto Kasei, PKHC of Dow Chemical Co., and BKR 2620 of Showa Union Gosei Corp.

Polyisocyanates can also be used as reactive resins, for example Coronate™ L of Nippon Polyurethane Inc., Desmodur™ N3300 or Mondur™ 489 of Bayer.

Further epoxy resins can contain, by preference, copolymers of acrylic acid esters with glycidol, for example glycidyl acrylate and glycidyl methacrylate with one or more copolymerizable vinyl compounds. Examples of such copolymers are 1:1 styrene/glycidyl methacrylate, 1:1 methyl methacrylate/glycidyl acrylate, and 62.5:24:13.5 methyl methacrylate/ethyl acrylate/glycidyl methacrylate.

Further usable epoxy resins are well known and contain epoxies such as, for example, epichlorohydrin; alkylene oxides, for example propylene oxide, styrene oxide; alkenyl oxides, for example butadiene oxide; glycidyl esters, for example ethyl glycidate.

Further usable epoxy resins are silicones having epoxide functionality, in particular cyclohexylepoxide groups, in particular those having a silicone basic framework. Examples are UV 9300, UV 9315, UV 9400, and UV 9425, all of which are supplied by GE Bayer Silicones.

In a preferred embodiment, the preparations according to the present invention encompass a mixture of several of the aforesaid epoxy resin systems.

Examples of such mixtures can encompass two or more molecular-weight distributions of epoxy-containing compounds, for example a low molecular weight (below 200), a moderate molecular weight (approx. 200 to 10,000), and a higher molecular weight (above approx. 10,000). Alternatively or additionally, the epoxy resin can contain a mixture of epoxy-containing materials of differing chemical nature (e.g. aliphatic or aromatic) or functionality (e.g. polar or nonpolar).

A "polyurethane resin system" is understood in the context of the present invention as a resin composition that is formed on the basis of polyurethanes.

A "benzoxazine resin system" is understood in the context of the present invention as a resin composition that is formed on the basis of benzoxazines.

An "acrylate resin system, cyanoacrylate resin system, triazine resin system, polyimide resin system, ester acrylate resin system" is understood in the context of the present invention as a resin composition that is formed on the basis of acrylates, cyanoacrylates, triazines, polyimides, and/or ester acrylates.

A further subject of the present invention is preparations containing
  0.5 wt % to 80 wt % initiator according to formula (I) or (II);
  0 wt % to 99.5 wt % additive resins;
  0 wt % to 50 wt % thermoplastic;
  0 wt % to 50 wt % further additives.

The preparations according to the present invention, which contain at least one initiator according to the present invention, are thermally and/or non-thermally curable.

The preparation according to the present invention is preferably an epoxy resin system that is non-thermally curable.

"Thermal" is understood in the context of the present invention as a curing operation initiated by external heat input, which does not encompass a non-thermal initiation brought about by deliberately and actively inputted non-thermal energy.

This heat input can be carried out, for example, by means of recirculating ovens or an oven equipped with infrared radiators as a heat source, or with microwave radiators.

Curing with the use of thermal heat is carried out by preference at 20 to 350° C, preferably at 50 to 250° C, for 10 seconds to 24 hours, by preference 30 minutes to 12 hours.

"Non-thermal" is understood in the present invention as a curing operation initiated by radiation, not encompassing a thermal initiation brought about by deliberately and actively inputted thermal energy. In this context, thermal energy that can result in or contribute to complete curing (polymerization) can result from the radiation-initiated curing (so-called post-curing).

Curing of the preparations or resin systems or resin system mixtures according to the present invention is preferably accomplished by rays having at least a wavelength of 1 mm, by preference at least 780 nm, preferably at least 1 nm, very particularly preferably at least 10 pm.

The preparations according to the present invention are preferably curable by means of radiation selected from X-rays, gamma rays, electron beams, UV rays, and/or microwave beams.

There are in this context no specific limitations on the radiation source. A mercury lamp, a halogen lamp, but also monochromatic radiation in the form of lasers can preferably be used as a source for UV rays.

If curing is accomplished using UV rays, the UV crosslinking then preferably takes place by means of short-wave ultraviolet irradiation in a wavelength region from 200 to 450 nm, in particular using high- or medium-pressure mercury lamps at an output from 80 to 240 W/cm.

As examples of the source of electron beams, it is possible to use a system for the utilization of thermal electrons generated by commercially obtainable tungsten filaments, a cold-cathode method that generates electron beams by passing a high-voltage pulse through a metal, and a secondary electron method that uses a metal electrode and secondary electrons generated by the collision of ionized gas molecules. Fissionable substances such as $Co^{60}$ can be used as a source of $\alpha$-rays, $\beta$-rays, and $\gamma$-rays. For $\gamma$-rays, a vacuum tube that brings about the collision of an accelerated electron with an anode can be used. The radiation can be used either individually or in combination with two or more radiation types. In the latter case, two or more radiation types can be used either simultaneously or at specific time intervals.

Curing with the use of radiation, in particular electron beams, is preferably carried out at 20 to 250° C, preferably at 80 to 100° C, in a time span from 5 seconds to 12 hours, preferably 8 seconds to 4 hours, very particularly preferably 10 seconds to 1 hour.

In a preferred embodiment, the radiation used to cure the preparations according to the present invention or one of the aforementioned resin systems is an ionizing radiation, preferably X-radiation and/or electron radiation.

In a further preferred embodiment, curing of the preparations or resin systems according to the present invention is accomplished by cationic polymerization, the polymerization preferably being initiated by the action of electron beams. Curing or polymerization by means of electron beams has the advantage that depending on the radiation energy selected, the beams almost completely penetrate the material to be cured, and homogeneous and complete curing can thus be better achieved. In addition, the high-energy radiation in the presence of cationic initiators releases a plurality of cations for polymerization.

A further subject of the present invention relates to epoxy resin systems containing at least one initiator according to the present invention. An epoxy resin system of this kind is preferably thermally and/or non-thermally curable, the radiation used to cure the epoxy resin system preferably being selected from X-rays, gamma rays, electron beams, UV rays, and/or microwave beams.

A curable preparation, preferably selected from an epoxy resin system that contains at least one initiator according to the present invention, is preferably curable at 3 eV to 25 MeV, in particular at 6 eV to 20 MeV, preferably at 1 keV to 15 MeV, very particularly at 1 keV to 10 MeV.

In a preferred embodiment, the epoxy resin system is cured with a freely selectable irradiation unit from 1 to 1000 kGy, by preference from 1 to 300 kGy, particularly preferably from 10 to 200 kGy.

The system is, in particular, curable at 132 kGy in four steps of 33 kGy each.

In a preferred embodiment, a combination of thermal and/or non-thermal curing can also be performed.

For example, firstly a thermal curing step can be carried out, and then a non-thermal one; or conversely first a non-thermal and then a thermal curing step can be performed.

If the thermal and non-thermal curing is to take place with oxygen or air excluded, the curing operation can also occur under a shielding gas. Suitable in principle as a shielding gas is any gas that behaves inertly with respect to the chemicals used (inert gas). Gases such as $N_2$, $CO_2$, or Ar are preferably appropriate in this context. Economical gases such as $CO_2$ and $N_2$ are, however, preferred. $CO_2$ has the advantage that it collects at the bottom of vessels and is thus easy to handle. Suitable shielding gases are, in particular, nontoxic and non-flammable.

A further subject of the present invention relates to the use of the initiators according to the present invention in the aforesaid preparations or epoxy resin systems as adhesives, composite materials, sealing compounds, materials, and for the coating of surfaces.

In a preferred embodiment, a preparation of this kind according to the present invention can be applied as a coating compound onto a surface and then cured. Suitable substrates are, in particular, preferably wood, paper, textile, leather, nonwoven fiber, plastics (polycarbonate, polymethacrylate, polystyrene, polyester, polyolefin, epoxy resins, melamine resins, triacetyl cellulose resins, ABS resins, AS resins, norbornene resins, etc.), glass, ceramic, paper, mineral construction materials such as cement blocks and fiber cement panels, metals, or coated metals. The substrate can also be a panel, a film or a three-dimensionally shaped element.

A variety of application methods can be utilized as a method for applying the preparation (in this case as a coating compound) onto the substrate, for example spraying, flow-coating, blade-coating, brushing, pouring, immersion, impregnation, dripping, rolling, sprinkle coating, or immersion coating.

In this context, the substrate to be coated can itself be stationary while the application device or system is moved. In some cases the substrate to be coated can also be moved, while the application system is stationary relative to the substrate or is moved in appropriate fashion.

In a further preferred embodiment, the initiators according to the present invention are used for the curing of materials, in particular shaped elements. Materials (shaped elements) of this kind that are manufactured using the initiators according to the present invention preferably exhibit a high level of mechanical stability and strength.

A further subject of the present invention is the use of the initiators according to the present invention in curable systems for, non-thermally initiated) curing being preferred.

Curable systems of this kind are preferably resin systems, for example epoxy resin systems, benzoxazine systems, polyurethane systems, acrylate resin systems, epoxy acrylate resin systems, cyanoacrylate resin systems, triazine resin systems, polyimide resin systems, ester acrylate resin systems, or thermoplastic resin systems, or further resin systems known to one skilled in the art. Epoxy resin systems are, however, preferred.

It is particularly preferred to use the initiators according to the present invention in curable systems that are non-thermally curable. These systems, preferably epoxy resin systems, are preferably curable using high-energy radiation such as, for example, electron radiation.

The initiators according to the present invention are, as a rule, easily soluble in the epoxy resin system. A high degree of crosslinking is furthermore evident after curing.

A further subject of the present invention relates to a method for curing a composition, encompassing the steps of
i) making available a preparation according to the present invention or an epoxy resin system according to the present invention;
ii) curing said preparation or epoxy resin system i) using a heat input that is sufficient to cure said preparation or said epoxy resin system i).

The heat input can be accomplished, for example, thermally or non-thermally; the heat input is by preference non-thermal.

A further subject of the present invention relates to a method for curing a composition, encompassing the steps of
i) making available a preparation according to the present invention or an epoxy resin system according to the present invention;
ii) curing said preparation or epoxy resin system i) using a radiation that is sufficient to cure said preparation or said epoxy resin system i).

The epoxy resin of said epoxy resin system is selected in particularly preferred fashion from the group made up of: glycidyl ethers of bisphenol A, epoxy-phenol novolacs, epoxy-cresol novolacs, epoxy compounds with bisphenol F, tetraglycidyl ethers of tetrakis(4-hydroxyphenyl)ethane, diglycidyl ethers of 9,9-bis(4-hydroxyphenyl)fluorene, glycidyl ethers of the condensation product of dicyclopentadiene and phenol, triglycidyl ethers of tris(hydroxyphenyl)methane, 3',4'-epoxycyclohexylmethyl-3,4-epoxycyclohexane carboxylate, diglycidyl esters of hexahydrophthalic acid, bis(3,4-epoxycyclohexylmethyl) adipate, high-molecular-weight diglycidyl ethers of bisphenol A or bisphenol F condensed with bisphenol A or bisphenol F, allyl glycidyl ethers, or mixtures thereof.

The present invention likewise relates to the cured product that is manufactured by curing the preparation according to the present invention or the epoxy resin system according to the present invention.

The cured product can by preference be cured non-thermally and/or thermally, and is preferably obtainable according to one of the above-described curing methods. Curing preferably occurred in accordance with one of said curing methods, in which a preparation according to the present invention or an epoxy resin system according to the present invention is made available, and curing of said preparation or said epoxy resin system is then accomplished by heat input, in particular by irradiation that is sufficient to cure said preparation or said epoxy resin system.

The cured product is preferably a coating, a film, a material, a composite material, an adhesive, or a sealing compound.

The Examples below explain the invention without, however, limiting it thereto.

EXAMPLES

Example 1

Synthesis of Silver Alkene Complexes and Further Complexes with $SbF_6^-$

The starting substance selected for the silver alkene complexes was commercially available $AgSbF_6$ (Aldrich, 98%; or Chempur, 95+%). Synthesis of the complexes was accomplished on the basis of methods known in the literature (H. W Qinn, R. L. Van Gilder, *Can. J. Chem.* 1970, 48, 2435; A. Albinati, S. V. Meille, G. Carturan, *J. Organomet. Chem.* 1979, 182, 269; H. Masuda, M. Munakata, S. Kitagawa, *J.*

*Organomet. Chem.*, 1990, 391, 131; A. J. Canty, R. Colton, *Inorg. Chim. Acta* 1994, 220, 99.) This involved dissolving $AgSbF_6$ in toluene or THF and reacting it with an excess of alkene, preferably four equivalents. The $\{[Ag(alkene)_a]SbF_6\}_n$ alkene complexes are poorly soluble and precipitate out of the reaction mixture, and can then be isolated by filtration. The substances are then dried under high vacuum. In the case of further metals and ligands, firstly the respective metal chloride was reacted with $AgSbF_6$ in a suitable solvent such as, for example, methanol, the precipitated AgCl was separated out by filtration, and the resulting solution of the metal hexafluoroantimonate was reacted with the respective ligand. The solvent was then removed and the compound was dried under high vacuum.

Example 2

Determining the Degree of Crosslinking

The degree of crosslinking of the (epoxy) resin was determined by FT-IR from the decrease in area under the epoxy band (915 cm$^{-1}$). The decrease in the epoxy band correlates with the degree of crosslinking. During crosslinking of the resin, the number of epoxy groups in the material decreases, as does also the area (ascertained by FT-IR) under the epoxy band. The benzene ring band (1505 cm$^{-1}$) was utilized as a reference band. The degree of crosslinking was then calculated using the following equation: Degree of crosslinking (%)=

$$\left[1 - \frac{(A_1/A_2)}{(A_3/A_4)}\right] * 100$$

A1: Area under epoxy band (915 cm$^{-1}$), cured
A2: Area under reference band (benzene ring band; 1505 cm$^{-1}$), cured
A3: Area under epoxy band (915 cm$^{-1}$), uncured
A4: Area under reference band (benzene ring band; 1505 cm$^{-1}$), uncured.

Example 3

Investigations of Fracture Mechanics

The statistical fracture toughness of the pure resin systems was determined under mode I loading per ISO 13586. A Zwick model Z020 universal tester was used to carry out the fracture-mechanics experiments. CT test articles having a sample width W of 33 mm served as test articles. The testing rate was 10 mm/min. All measurements were carried out at 23° C and 50% relative humidity.

Example 4

Thermal Curing and Electron Beam (EB) Curing of a Resin Composition Containing an Initiator According to the Present Invention The resins or resin formulations, which were liquid, viscous, or solid at room temperature (69.3 wt % DEN431+29.7 wt % DEN438) were mixed at room temperature with the corresponding initiator (1 wt % $\{[Ag(1,7\text{-octadiene})_{1.5}]SbF6\}_\infty$), heated to a maximum of 80° C, and stirred until the initiator was completely dissolved in the resin. The mixture was then cooled to room temperature.

a) Electron Beam-Initiated Curing

For electron-beam curing of the resin samples as manufactured above, the resin formulation is firstly degassed at a maximum of 80° C in a vacuum drying cabinet, poured into molds (approx. 20 cm×20 cm×4 mm), and the surface is smoothed with a wooden rod. Complete freedom from bubbles is important here. The specimens are then passed through the electron-beam system (10 MeV), curing being performed in four steps in each of which a dose of 33 kGy is introduced (total 132 kGy).

b) Thermally Initiated Curing

For thermal curing of the resin samples that were manufactured, the hot (80° C) resin mixture is poured into aluminum molds (also heated to 80° C), the surface is then smoothed using a wooden rod, and degassing is then performed for 45 to 60 minutes in a vacuum drying cabinet (at 80° C). The samples are then cured in a heating oven in accordance with the following temperature program:
1) from 25° C to 200° C at 1° C/min
2) at 200° C for 2 hours
3) from 200° C to 25° C at 2° C/min
For improved release of the cured resin samples from the mold, they are previously coated with a thin layer of Frekote-700NC mold release agent (Henkel Loctite).

TABLE 1

Results of electron beam (EB) curing and thermal curing

|  | EB curing | Thermal curing |
|---|---|---|
| Degree of crosslinking (%) | 90.8 | 94.8 |
| Tg tan delta (° C.) | 190 | 211 |
| Tg loss (° C.) | 160 | 187 |
| Tg onset log (° C.) | 153 | 180 |
| E modulus (MPa) | 3600 | 3300 |
| $K_{Ic}$ (MPa · m1/2) | 0.466 | 0.421 |

Table 1 shows that the silver salt according to the present invention initiates a cationic polymerization in the resin as a result of both electron radiation and thermal energy, and that a high degree of crosslinking is achieved. It is also evident that after curing, the resins exhibit high values for E modulus and fracture toughness.

Example 5

UV Curing of a Resin Composition Containing an Initiator According to the Present Invention To carry out UV-initiated curing, a DGEBA resin (DER 331P of Dow Chemical Co.) had 1 wt % $\{[Ag(1,7\text{-octadiene})_{1.5}]SbF_6\}_\infty$ added to it and was homogenized at max. 80° C while being stirred. The composition obtained was blade-coated at approx. 30° C, at a layer thickness of approx. 1 mm, onto aluminum panels (Al 2024 sheets) that had previously been cleaned with acetone, and then cured using UV radiation (H radiator of Fusion system, 100% power, 30 cm distance).

TABLE 2

Results of UV curing

| | Degree of crosslinking (%) | | |
| Irradiation | Upper side | Lower side | Tg (DSC) (° C.) |
|---|---|---|---|
| 15 s | 64 | 29 | |
| 30 s | 79 | 40 | 57 |

TABLE 2-continued

Results of UV curing

| Irradiation | Degree of crosslinking (%) | | Tg (DSC) (° C.) |
|---|---|---|---|
| | Upper side | Lower side | |
| 60 s | 87 | 59 | 89 |
| 120 s | 87 | 59 | 87 |
| 180 s | 89 | 59 | 83 |
| 240 s | 91 | 62 | 89 |

The results show that the silver salt according to the present invention is also UV-active, and initiates a cationic polymerization of epoxy resins.

With UV irradiation as well, the silver salt therefore results in high degrees of crosslinking at the surface of the resin formulations. The degree of crosslinking of the surface rises with irradiation time. The glass transition temperature (Tg) of the formulations likewise rises with irradiation time. The degrees of crosslinking on the lower side of the samples are lower as compared with the surface data that were ascertained on the side facing the radiation source; this can be explained by the fact that the radiation penetration depth for UV curing is generally low (because the radiation energy is low).

Example 6

Electron Beam Curing Using Various Initiators

TABLE 3

Results of electron beam curing

| Initiator | Wt % | Resin Type | Wt % | Tg (tan δ) | E modulus MPa | Degree of crosslinking (%) |
|---|---|---|---|---|---|---|
| Ag[(cyclohepta-1,3,5-triene)$_a$]SbF$_6$ | 2 | 1 | | 177 | 3500 | 95.5 |
| Ag[(cyclohepta-1,3,5-triene)$_a$]SbF$_6$ | 2 | 2 | | 233 | 3000 | 96.3 |
| Ag[(cyclohepta-1,3,5-triene)$_a$]SbF$_6$ | 1 | 1 | 99 | 182 | 3400 | 93.6 |
| Ag[(cyclohepta-1,3,5-triene)$_a$]SbF$_6$ | 1 | 1 | 69.3 | 201 | 3400 | 93.2 |
| | | 2 | 29.7 | | | |
| Ag[(cyclohexene)$_a$]SbF$_6$ | 1 | 1 | 99 | 185 | 3500 | 91.1 |
| Ag[(cyclohexene)$_a$]SbF$_6$ | 2 | 1 | 98 | 190 | 3100 | 91.4 |
| Ag[(cyclohexene)$_a$]SbF$_6$ | 2 | 2 | 98 | 201 | 3500 | 92.4 |
| Ag[(1,7-octadiene)$_a$]SbF$_6$ | 1 | 1 | 99 | 190 | 3000 | 94.4 |
| Ag[(1,7-octadiene)$_a$]SbF$_6$ | 1.5 | 1 | 98 | 175 | 3100 | 94.3 |
| Ag[(1,7-octadiene)$_a$]SbF$_6$ | 2 | 1 | 98 | 190 | 3100 | 95.1 |
| Ag[(COD)$_2$]SbF$_6$ | 2 | 1 | 98 | 187 | 3400 | 96.8 |
| Ag[(COD)$_2$]SbF$_6$ | 3 | 1 | 97 | 183 | 3500 | 96.4 |
| Ag[(1,7-octadiene)$_a$]SbF$_6$ | 1.5 | 2 | 98 | 211 | 3800 | 95.0 |
| Ag[(1,7-octadiene)$_a$]SbF$_6$ | 2 | 2 | 98 | 217 | 3300 | 96.9 |
| Ag[(1,7-octadiene)$_a$]SbF$_6$ | 1 | 1 | 49.5 | 203 | 3900 | 92.4 |
| | | 2 | 49.5 | | | |
| Ag[(1,7-octadiene)$_a$]SbF$_6$ | 2 | 1 | 49 | 201 | 3100 | 96.8 |
| | | 2 | 49 | | | |
| Ag[(1,7-octadiene)$_a$]SbF$_6$ | 1 | 1 | 69.3 | 190 | 3600 | 90.8 |
| | | 2 | 29.7 | | | |
| Ag[(1,7-octadiene)$_a$]SbF$_6$ | 2 | 1 | 69.3 | 199 | 3500 | 95.1 |
| | | 2 | 29.4 | | | |
| Ag[(1,7-octadiene)$_a$]SbF$_6$ | 1 | 1 | 89.1 | 185 | 3000 | 91.8 |
| | | 2 | 9.9 | | | |
| Ag[(1,7-octadiene)$_a$]SbF$_6$ | 1.5 | 1 | 68.9 | 198 | 3700 | 96.1 |
| | | 2 | 29.5 | | | |
| Ag[(1,7-octadiene)$_a$]SbF$_6$ | 2 | 1 | 88.2 | 188 | 3800 | 93.5 |
| | | 2 | 9.8 | | | |
| Ag[(1,7-octadiene)$_a$]SbF$_6$ | 1 | 1 | 99 | 184 | 3600 | 99.2 |
| Ag[(1,7-octadiene)$_a$]SbF$_6$ | 1 | 2 | 99 | 204 | 3600 | 99.4 |
| Cyracure UV 6976* | 3 | 1 | 97 | 180 | 3300 | 91.0 |
| Cyracure UV 6976* | 3 | 2 | 96 | 217 | 3200 | 83.8 |
| Deuteron UV 1242** | 2 | 1 | 98 | 162 | 3500 | 76.1 |
| Rhodorsil 2074*** | 0.5 | 1 | 99 | 200 | 3300 | 93.7 |
| Rhodorsil 2074*** | 1 | 1 | 9 | 205 | 3500 | 96.4 |
| Rhodorsil 2074*** | 0.5 | 2 | 99 | 215 | 4300 | 97.4 |
| Rhodorsil 2074*** | 1 | 2 | 99 | 233 | 3500 | 98.2 |
| Rhodorsil 2074*** | 1 | 1 | 69.3 | 211 | 3600 | 97.0 |
| | | 2 | 29.7 | | | |

*Dow
**Deuteron
***Rhodia
Resin type 1 = DEN431P Novolac of Dow (EEW: 176 ± 3, viscosity 1400 ± 300 mPa · s, 52° C.)
Resin type 2 = DEN438 Novolac of Dow (EEW: 179 ± 3, viscosity 35,500 ± 3100 mPa · s, 52° C.)

Example 7

Shelf Stability

Shelf stability was determined by measuring the relative viscosity using a pot time measuring instrument at 80° C.

TABLE 4

| Relative viscosity of DEN438 resin with 1 wt % initiator | | |
|---|---|---|
| | Viscosity (η) | |
| Time (minutes) | Rhodorsil 2074 | {Ag[(1,7-octadiene)$_{1.5}$]SbF$_6$}∞ |
| 650 | 0 | 0.6 |
| 700 | 14.7 | 1.9 |
| 750 | 62.9 | 4.6 |

Example 8

Solubility of Initiators in the Resin

A determination of the solubilities of the initiators according to the present invention and the initiators of the existing art in DEN 431 resin was performed at 70° C within 2 hours.

TABLE 5

| Solubility of 1 wt % initiator in resin | |
|---|---|
| Initiator | Solubility |
| {Ag[(cycloheptatriene)$_{1-4}$]SbF$_6$}∞ | ++ |
| [Ag(1,5-cyclooctadiene)$_2$]SbF$_6$ | + |
| {[Ag(1,7-octadiene)$_{1.5}$]SbF$_6$}∞ | ++ |
| Cyracure UV 6976 | ++ |
| Rhodorsil 2074 | ++ |
| Deuteron UV 1242 | ++ |

Legend:
− = poorly soluble
+ = readily soluble
++ = very readily soluble.

The invention claimed is:

1. An initiator of the general formula (I)

{[M(L)$_a$]X$_b$}$_n$  (I), wherein M=a Ag metal cation,
L=a ligand having at least one double and/or triple bond, selected from the group consisting of propene, 1-butene, 1-pentene, 1-hexene, 1-octene, 1-decene, isoprene, norbornene, cyclohexene, cyclooctene, cyclodecene, 1,4-cyclohexadiene, 4-vinylcyclohexene, trans-2-octene, styrene, 5-norbornene-2-carboxylic acid, butadiene, 1,5-hexadiene, 1,6-heptadiene, 1,7-octadiene, 1,9-decadiene, sorbic acid ethyl ester, 1,3-cyclohexadiene, 1,3-cyclooctadiene, 1,5-cyclooctadiene, norbornadiene, dicyclopentadiene, cycloheptatriene, trans,trans,trans-1,5,9-cyclododecatriene, trans,trans,cis-1,5,9-cyclododecatriene, cyclooctatetraene, squalene, diallyl carbonate, diallyl ether, diallyldimethylsilane, nopol, cyclopentadiene, ethyl vinyl ether, limonene, 1,2-dihydronaphthalene, cinnamic acid ethyl ester, ethyl acrylate, ethyl methacrylate, stilbene, oleic acid methyl ester, linoleic acid methyl ester, linolenic acid methyl ester, diphenylacetylene, dimethylacetylene, 3-hexine, 1,8-cyclotetradecadiine, propargyl alcohol, vinylacetylene, 1-phenylpropine, and 1,8-nonadiine,
X=a counterion selected from the group consisting of hexafluoroantimonate (SbF$_6^-$), hexafluorophosphate (PF$_6^-$), hexafluoroaluminate (AlF$_6^{3-}$), trifluoromethanesulfonate (CF$_3$SO$_3^-$), nitrate (NO$_3^-$), hexafluoroarsenate (AsF$_6^-$), tetrakis(pentafluorophenylborate) (B[C$_6$F$_5$]$_4^-$), tetrakis[3.5-bis (trifluoromethyl)phenyl]borate (B[C$_6$H$_3$(CF$_3$)$_2$]$_4^-$), tetraphenylborate (B[C$_6$H$_5$]$_4^-$), hexafluorotitanate (TiF$_6^{2-}$), hexafluorogermanate (GeF$_6^{2-}$), hexafluorosilicate (SiF$_6^{2-}$), hexafluoronickelate (NiF$_6^{2-}$), and hexafluorozirconate (ZrF$_6^{2-}$), and
a=1 to 10,
b=1 to 10,
n=1 to 20,000.

2. The initiator according to claim 1, wherein the counterion (X) is hexafluoroantimonate (SbF$_6^-$)

3. An initiator according to claim 1, wherein the initiator is selected from the group consisting of Ag(cyclohexene) SbF$_6$, Ag(cyclooctene) SbF$_6$, Ag(cyclododecene) SbF$_6$, Ag(trans-2-octene) SbF$_6$, Ag(styrene) SbF$_6$, Ag(5-norbornene-2-carboxylic acid) SbF$_6$, Ag(1,5-hexadiene) SbF$_6$, Ag(1,7-octadiene) SbF$_6$, Ag(1,7-octadiene)]SbF$_6$, Ag(1,9-decadiene) SbF$_6$, Ag(sorbic acid ethyl ester) SbF$_6$, Ag(1,3-cyclohexadiene) SbF$_6$, Ag(1,3-cyclooctadiene) SbF$_6$, Ag(1,5-cyclooctadiene) SbF$_6$, Ag(norbornadiene) SbF$_6$, Ag(dicyclopentadiene) SbF$_6$, Ag(cycloheptatriene) SbF$_6$, Cu(1,7-octadiene) SbF$_6$, Cu(1,5-cyclooctadiene) SbF$_6$, Ag(1R-(−)-nopol) SbF$_6$, Ag(allyl glycidyl ether) SbF$_6$, Ag(trans,trans,cis-1,5,9-cyclododecatriene) SbF$_6$, Ag(trans,trans,trans-1,5,9-cyclododecatriene) SbF$_6$, Ag(cyclooctatetraene) SbF$_6$, and Ag(squalene) SbF$_6$.

4. A composition comprising at least one initiator of formula (Ia), wherein the initiator is represented by general formula (Ia)

{[M(L)$_a$]X$_b$}$_n$  (Ia), wherein M=a metal cation selected from the group consisting of Ag, Mg, Cu and Al,
L=a ligand having at least one double and/or triple bond, selected from the group consisting of propene, 1-butene, 1-pentene, 1-hexene, 1-octene, 1-decene, isoprene, norbornene, cyclohexene, cyclooctene, cyclodecene, 1,4-cyclohexadiene, 4-vinylcyclohexene, trans-2-octene, styrene, 5-norbornene-2-carboxylic acid, butadiene, 1,5-hexadiene, 1,6-heptadiene, 1,7-octadiene, 1,9-decadiene, sorbic acid ethyl ester, 1,3-cyclohexadiene, 1,3-cyclooctadiene, 1,5-cyclooctadiene, norbornadiene, dicyclopentadiene, cycloheptatriene, trans,trans,trans-1,5,9-cyclododecatriene, trans,trans,cis-1,5,9-cyclododecatriene, cyclooctatetraene, squalene, diallyl carbonate, diallyl ether, diallyldimethylsilane, nopol, cyclopentadiene, ethyl vinyl ether, limonene, 1,2-dihydronaphthalene, cinnamic acid ethyl ester, ethyl acrylate, ethyl methacrylate, stilbene, oleic acid methyl ester, linoleic acid methyl ester, linolenic acid methyl ester, diphenylacetylene, dimethylacetylene, 3-hexine, 1,8-cyclotetradecadiine, propargyl alcohol, vinylacetylene, 1-phenylpropine, and 1,8-nonadiine,
X=a counterion selected from the group consisting of hexafluoroantimonate (SbF$_6^-$), hexafluorophosphate (PF$_6^-$), boron tetrafluoride (BF$_4^-$), hexafluoroaluminate (AlF$_6^{3-}$), trifluoromethanesulfonate (CF$_3$SO$_3^-$), nitrate (NO$_3^-$), hexafluoroarsenate (AsF$_6^-$), tetrakis(pentafluorophenylborate) (B[C$_6$F$_5$]$_4^-$), tetrakis[3.5-bis(trifluoromethyl)phenyl]borate (B[C$_6$H$_3$(CF$_3$)$_2$]$_4^-$), tetraphenylborate (B[C$_6$H$_5$]$_4^-$), hexafluorotitanate (TiF$_6^{2-}$), hexafluorogermanate ($GeF_6^{2-}$), hexafluorosilicate ($SiF_6^{2-}$), hexafluoronickelate ($NiF_6^{2-}$), and hexafluorozirconate ($ZrF_6^{2-}$), and a=1 to 10,
b=1 to 10,
n=1 to 20,000, and a resin system selected from the group consisting of epoxy resin systems, benzoxazine resin systems, polyurethane resin systems, acrylate resin systems, epoxy acrylate resin systems, cyanoacrylate resin systems, triazine resin systems, polyimide resin systems, ester acrylate resin systems, and thermoplastic resin systems.

5. The composition according to claim 4, wherein the concentration of the initiators is 0.01 to 10 wt %, based on the entire composition.

6. The composition according to claim 4, wherein the composition is curable.

7. The composition according to claim 4, wherein the preparation is curable by exposure to radiation selected from the group consisting of X-rays, gamma rays, electron beams, UV rays, and microwave beams.

8. The composition of claim 4, wherein the resin system is an epoxy resin system.

9. A method for curing a composition, encompassing the steps of
  i) making available a composition according to claim 4;
  ii) curing said composition using either a heat input that is sufficient to cure said composition or radiation that is sufficient to cure said composition.

10. A cured product that is manufactured by curing a composition according to claims 4.

11. The cured product according to claim 10, wherein the cured product has been cured non-thermally and/or thermally.

12. The cured product according to claim 10, wherein the cured product is selected from the group consisting of a coating, a film, a material, a composite material, an adhesive, and a sealing compound.

* * * * *